(12) United States Patent
Jimenez et al.

(10) Patent No.: US 8,156,602 B2
(45) Date of Patent: Apr. 17, 2012

(54) GENERATING A CHEMICAL AGENT IN SITU

(75) Inventors: Eduardo J. Jimenez, Manalapan, NJ (US); Robert Dickson, Belle Mead, NJ (US); Douglas J. Hohlbein, Pennington, NJ (US); Heng Cai, Skillman, NJ (US); Sharon Kennedy, Randallstown, MD (US); Thomas Mintel, Rahway, NJ (US); Bruce M. Russell, Howell, NJ (US)

(73) Assignee: Colgate-Palmolive Company, New York, NY (US)

( * ) Notice: Subject to any disclaimer, the term of this patent is extended or adjusted under 35 U.S.C. 154(b) by 275 days.

(21) Appl. No.: 11/549,497

(22) Filed: Oct. 13, 2006

(65) Prior Publication Data

US 2007/0212665 A1    Sep. 13, 2007

Related U.S. Application Data

(60) Provisional application No. 60/726,732, filed on Oct. 14, 2005.

(51) Int. Cl.
  *A46B 9/04* (2006.01)
(52) U.S. Cl. ................................. 15/167.1
(58) Field of Classification Search ......... 15/105, 15/167.1; 433/32, 173, 176, 169, 174, 175, 433/201.1, 215, 216; 205/687; 422/186.18; 604/19–20, 48, 73, 77; 607/79; 606/32–34, 606/41–42; 132/148, 271; 424/53, 616
See application file for complete search history.

(56) References Cited

U.S. PATENT DOCUMENTS

| | | | |
|---|---|---|---|
| 2,834,344 A | 5/1958 | Kanai |
| 3,478,741 A | 11/1969 | Simor |
| 3,520,297 A | 7/1970 | Bechtold |
| 4,502,497 A | 3/1985 | Siahou |
| 4,526,570 A | 7/1985 | Nakagawa et al. |
| 4,665,921 A | 5/1987 | Teranishi et al. |
| 4,691,718 A | 9/1987 | Sakuma et al. |
| 4,726,806 A | 2/1988 | Hukuba |

(Continued)

FOREIGN PATENT DOCUMENTS

CN   2323750 Y   9/1997

(Continued)

OTHER PUBLICATIONS

Machine translation of JP 5-23219.*

(Continued)

*Primary Examiner* — Todd Manahan
*Assistant Examiner* — Matthew Nelson
(74) *Attorney, Agent, or Firm* — Amy M. Fernandez

(57) ABSTRACT

A device for generating a chemical agent in situ on an as-needed basis via the application of an electrical potential across a pair of conductors in communication with an electrolyte. The device may be a toothbrush that generates chemical agents in a user's mouth by applying an electrical potential to an electrolyte such as saliva and/or a dentifrice located therein. The chemical agents may include ozone, hydrogen peroxide, peroxide, chlorine and/or hypochlorite. The toothbrush may include a voltage source and a first set of electrodes for applying an electrical potential to the electrolyte. The toothbrush may also include a second set of electrodes disposed about an anode of the first set of electrodes. The first and second sets of anodes cooperate to produce ions, peroxides, ozone and/or other chemical agents via the application of electrical potential to the electrolyte.

44 Claims, 10 Drawing Sheets

U.S. PATENT DOCUMENTS

| | | | |
|---|---|---|---|
| 4,969,868 A * | 11/1990 | Wang | 604/20 |
| 5,113,102 A | 5/1992 | Gilmore | |
| 5,115,533 A | 5/1992 | Hukuba | |
| 5,133,102 A | 7/1992 | Sakuma | |
| 5,804,053 A * | 9/1998 | Vaccaro et al. | 205/138 |
| 5,921,251 A * | 7/1999 | Joshi | 132/112 |
| 6,007,686 A * | 12/1999 | Welch et al. | 204/230.2 |
| 6,135,126 A * | 10/2000 | Joshi | 132/308 |
| 6,139,809 A | 10/2000 | Rodden | |
| 6,343,400 B1 | 2/2002 | Massholder et al. | |
| 6,496,998 B2 | 12/2002 | Moran | |
| 2002/0177107 A1 | 11/2002 | Moran | |
| 2003/0054321 A1 | 3/2003 | Moran | |
| 2005/0061344 A1 | 3/2005 | Taylor et al. | |
| 2006/0070195 A1 * | 4/2006 | Morita et al. | 15/105 |

FOREIGN PATENT DOCUMENTS

| | | |
|---|---|---|
| DE | 31 14324 | 8/1982 |
| DE | 3114324 A1 * | 8/1982 |
| EP | 0 357 852 | 3/1990 |
| EP | 0613636 | 9/1994 |
| EP | 1350442 | 10/2003 |
| GB | 2 309 378 | 7/1997 |
| GB | 2371217 | 7/2002 |
| JP | 04215706 A * | 8/1992 |
| JP | 2005-205068 | 8/2005 |
| RU | 12509 | 1/2000 |
| RU | 2170051 | 7/2001 |
| WO | 92/10113 | 6/1992 |
| WO | 93/16001 | 8/1993 |
| WO | 01/19729 | 3/2001 |
| WO | 01/30198 | 5/2001 |
| WO | WO 03/037210 | 5/2003 |
| WO | WO 03/043459 | 5/2003 |

OTHER PUBLICATIONS

International Search Report and Written Opinion in International Application No. PCT/US06/040344, mailed Feb. 16, 2007.

* cited by examiner

GENERATING A CHEMICAL AGENT IN SITU

CROSS REFERENCE TO RELATED APPLICATION

This application claims the benefit of priority to U.S. application Ser. No. 60/726,732 filed Oct. 14, 2005, the contents of which are incorporated herein.

FIELD OF THE INVENTION

The present invention relates to a device and method for generating a chemical agent in situ. In particular, the present invention relates to a device, such as a toothbrush, that generates a chemical agent in situ by applying an electrical potential across a pair of conductors in communication with an electrolytic solution.

BACKGROUND OF THE INVENTION

Oral care products include a variety of chemical agents that perform a range of functions. For instance, toothpastes, mouthwashes and whiteners include chemical agents that help to clean teeth, kill bacteria, freshen breath and/or whiten teeth. These products typically cooperate with a device such as a toothbrush, an applicator device, or a tongue scraper, to perform their intended functions. In addition, chemical agents in these products may provide secondary benefits such as providing pleasing flavors or odors.

Many oral care products are configured to be multi-functional. For example, conventional toothpaste is configured to assist with multiple functions, such as cleaning teeth, fighting tartar, providing fluoride protection, freshening breath and whitening teeth. As such, the concentrations and types of chemical agents therein are limited by chemical interaction considerations and by chemical stability considerations thereof during prolonged storage.

Oral care products that are directed to whitening teeth include an oxidizing agent as the primary active ingredient, such as hydrogen peroxide. These products are formulated into liquids, pastes or gels for application to users' teeth. Upon storage, these products lose their whitening efficacy over time. In addition, these products have a brief period of efficacy when applied to the teeth in the oral cavity. For example, saliva contains high concentrations of the enzyme catalase, which on contact rapidly decomposes hydrogen peroxide into gaseous oxygen and water and so that there is only transitory contact of the peroxide whitening agent with the teeth. In addition, the low viscosities of aqueous peroxide solutions do not allow the peroxide whitening agent to remain in contact with the teeth for as long as is necessary to effect substantive whitening, because of the constant flushing effects of salivary secretions. As such, it is desirable to have high concentrations of oxidizing agents or effective oxidizing agents applied directly to teeth.

Toothbrushes are known that generate beneficial agents, including oxidizing agents when needed luring brushing. U.S. Pat. No. 5,921,251 to Joshi discloses a toothbrush that generates beneficial oral care agents within the toothbrush when needed during brushing and that delivers them to the user's teeth once they are generated. The Joshi toothbrush generates within the toothbrush handle a fluid containing an oxidizing agent, which it delivers to the toothbrush bristles. The agent is generated via an electrochemical gas-generating cell within the toothbrush handle or via a photoelectrochemical cell within the handle.

The Joshi toothbrush does not generate its beneficial agents in situ at the application site, but instead generates them internally and subsequently transfers them to the application site. The Joshi toothbrush generates its beneficial agents from an electrolyte stored within the toothbrush handle (using its electrochemical gas generator), or it generates them from a catalyst stored within the handle via the application of light from an internal light source.

Toothbrushes are also known that generate ionized molecules by applying a voltage across electrodes on a toothbrush handle in contact with a dentifrice slurry. U.S. Pat. No. 6,496,998 to Moran; U.S. Patent Publication 2003/0054321 to Moran; and U.S. Patent Publication 2002/0177107 to Moran each discloses a toothbrush that generates weak acids of fluoride via the application of an electric charge to electrodes on the toothbrush handle in contact with an aqueous dentifrice containing sodium fluoride. The Moran toothbrushes generate fluoride ions by applying a three-volt electric charge to the aqueous slurry containing sodium fluoride. It also generates diatomic oxygen and hydrogen ions via the electrolysis of water in the slurry from same electric charge. The hydrogen ions combine with the fluoride ions to produce weak acids of fluoride (HF), which reduce the amount of acid-producing bacteria in plaque. The Moran references do not disclose a toothbrush that generates oxidizing agents other than oxygen itself via the application of an electric charge to an electrolyte. Further, the Moran references disclose generating oxygen and hydrogen ions along the toothbrush handle and do not disclose generating oxidizing agents in situ at the application site within a field of cleaning elements.

SUMMARY OF THE INVENTION

The present invention provides a device that generates a chemical agent in situ via the application of an electrical potential across a pair of conductors in communication with an electrolytic solution. In one embodiment, the device is a toothbrush that generates chemical agents in a user's mouth by applying an electrical potential to an aqueous electrolyte, such as a toothpaste slurry, located therein. The chemical agents may include ozone, hydrogen peroxide, or other substances depending on factors such as the composition of the electrolyte and the construction of the toothbrush. The toothbrush includes a voltage source and a first set of electrodes for applying an electrical potential to the aqueous electrolyte.

In a low voltage construction, the toothbrush can generate ions from the aqueous electrolyte, such as calcium ions, hydrogen ions, hydroxide ions and fluoride ions. In a higher voltage construction, the toothbrush can generate hydrogen peroxide and ozone. In another low voltage construction, the toothbrush includes a second set of electrodes disposed about an anode of the first set of electrodes. The first and second sets of anodes cooperate to produce hydrogen, oxygen, ions, peroxides and/or ozone via the application of a low voltage to the aqueous electrolyte and to oxygen generated thereby. In a high voltage construction, the toothbrush can generate hydrogen, oxygen and ozone.

Other aspects of the present invention provide methods for generating chemical agents in situ within a field of cleaning elements of the oral care device. These and other aspects are addressed in relation to the figures and related description.

DETAILED DESCRIPTION OF THE INVENTION

A toothbrush 100 is shown in FIGS. 1-4 for generating a chemical agent in situ. As used herein, in situ means at an application site of the chemical agent, such as within a field of cleaning elements of an applicator device, and/or proximate a location of use for a chemical agent. Although toothbrush embodiments are shown in the figures herein, it is understood that aspects of the invention may be applicable to a wide variety of devices that can apply or work with chemical agents. For example, aspects of the invention may be applicable to tongue scrapers, tooth whitener applicators, gum stimulators, etc. Further, aspects of the invention may be applicable for a wide variety of other powered devices. For instance, other brushes such as scrub brushes may take advantage of aspects of the invention, as could cleaning devices such as sponges (e.g., to generate a cleaning agent), grooming devices such as razors (e.g., to generate a skin-softening agent), health-care devices such as devices for cleaning a wound (e.g., to generate a sanitizing agent), sanitizing devices such as dishwashers or laundry washers (e.g., to generate a bleach), etc.

Figure 1:
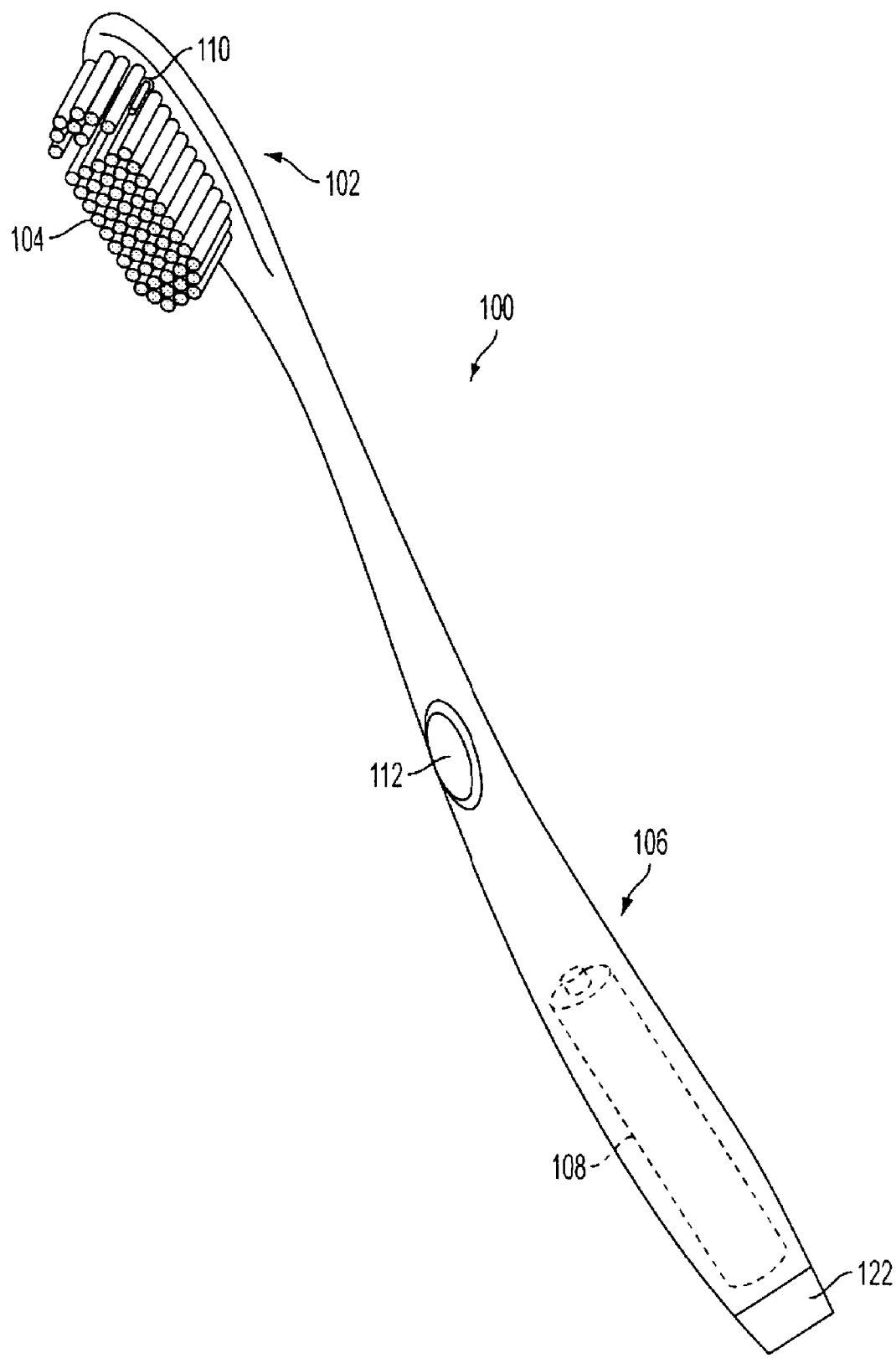
FIG. 1 is a perspective view a toothbrush according to an embodiment of the present invention.

As generally shown in FIG. 1, toothbrush 100 has a head portion 102 at one end supporting cleaning elements such as bristles 104, and a handle portion 106 at the opposite end. The handle portion 106 has one or more compartments for containing a voltage source 108, such as a battery or a capacitor. The voltage source 108 is electrically connected to a set of electrodes 110 via a switch 112. The electrodes 110 are located at the head portion 102 within a field of cleaning elements, which in the present configuration primarily include bristles 104. At such a location, electrodes 110 are able to make contact with an electrolyte within a user's mouth and to generate chemical agents in situ at the application site of the agents. The electrolyte may include saliva alone, a dentifrice in the presence of saliva, and/or a mixture of saliva, dentifrice and conductivity agents, such as salts, which increase the conductivity of an aqueous solution. Although shown as a toothbrush with a non-moving head, it is understood that toothbrush 100 could have a moving head and may have a variety of configurations.

The voltage source 108 is electrically connected to electrodes 110 for providing an electrical potential to the electrodes. As discussed in more detail below, applying the electrical potential in the presence of an electrolyte acts to generate chemical agents in situ. In other words, the toothbrush produces chemical agents while in the user's mouth via electrolysis at the application site of the agents.

Toothbrush 100 can generate the chemical agents in a variety of ways depending on factors such as the configuration of the toothbrush, the electrical potential provided to electrodes 110, the composition of the electrolyte, the composition of electrodes 110, etc. For instance, in the presence of saliva alone, toothbrush 100 can generate hydrogen, oxygen, peroxide and ozone depending on factors like the voltage applied to electrodes 110, the distance separating the cathode 114 and the anode 116 of electrodes 110 (see FIG. 3), and the composition of the electrodes. In the presence of ionic compounds such as sodium chloride, potassium chloride, or calcium carbonate that may be contained in an aqueous dentifrice, chemical agents such as chlorine or calcium can be generated. In another example, in the presence of a dentifrice containing an activatable chemical agent that is stored in an inactive state, the chemical agent can be generated by being activated via the electric charge.

Figure 2:
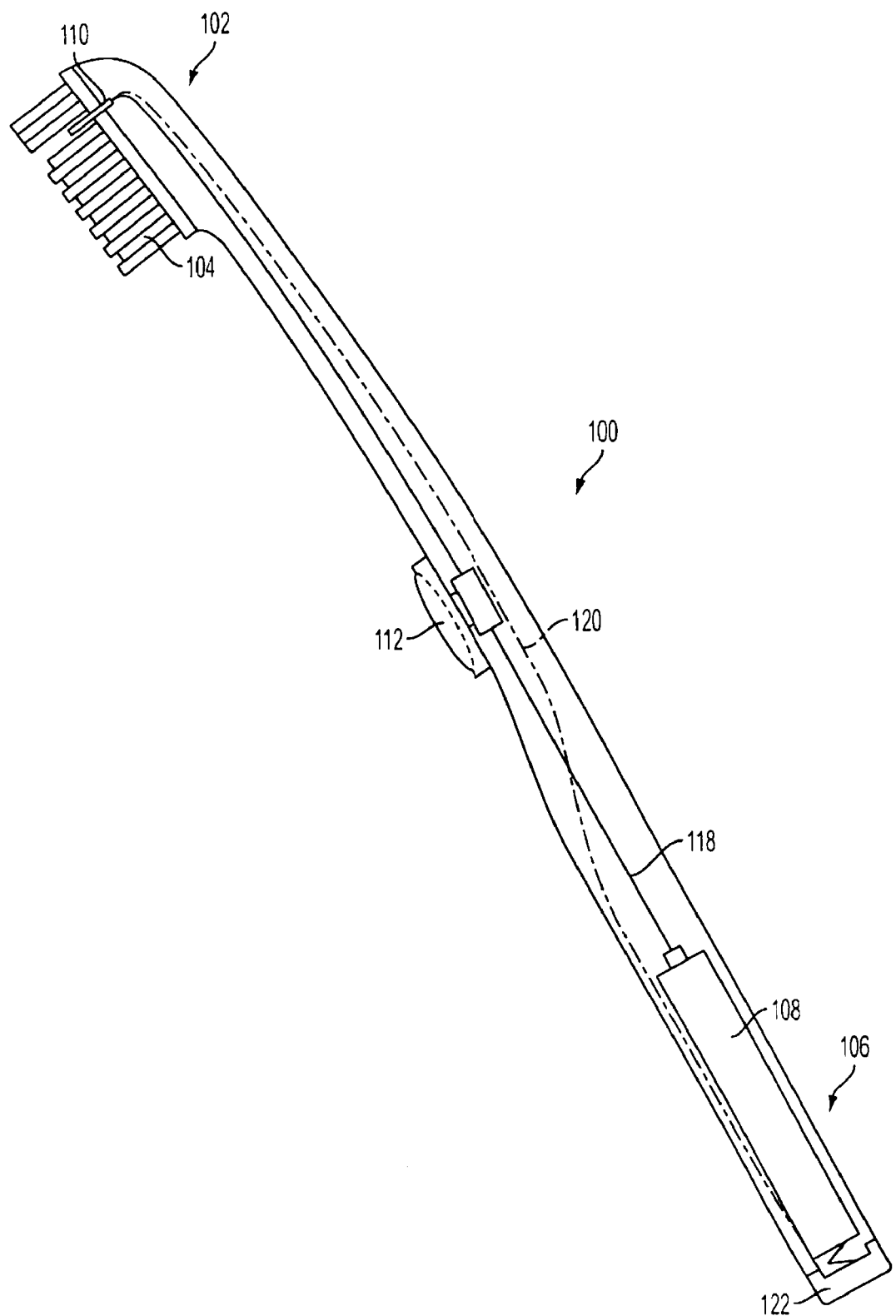
FIG. 2 is a cross-sectional view of the toothbrush of FIG. 1.

As shown in FIG. 2, voltage source 108 is connected to electrodes 110 via a positive line 118 and a negative line 120. The positive line 118 is connected to anode 116 (see FIG. 3) and negative line 120 is connected to cathode 114. Switch 112 is shown electrically connected to positive line 118 for interrupting its electrical connection with anode 116 as desired by the user. It is understood, however, that switch 112 could be configured to electrically interrupt negative line 120 or both lines. Further, it is understood that switch 112 could have multiple settings for various voltage settings that may be appropriate for different uses, for use with different electrolytes, and/or for generating different chemical agents depending upon the applied voltage setting. For instance, a high voltage setting may be appropriate for use with saliva alone to produce ozone from water as discussed in more detail below, and a low voltage setting may be appropriate for use with a dentifrice containing potassium chloride to produce chlorine in situ as also discussed below. In another example, a low voltage setting may produce one or more first chemical agents at a low voltage, such as oxygen and hydrogen ions in the presence of an aqueous dentifrice, and a high voltage setting may produce one or more second chemical agents at a high voltage, such as ozone in addition to oxygen and hydrogen ions. The voltages could be controlled using known voltage regulation techniques, such as by adding a potentiometer, transformer and/or voltage regulator to the electrical circuit.

Voltage source 108 may be a replaceable battery, such as a conventional AAA battery, which can be removed via cap 122 that provides access to a battery compartment. The voltage source may also be a built-in electrical storage device, such as a capacitor or rechargeable battery, and it may be a built-in disposable battery for a disposable toothbrush configuration. In other configurations, voltage source 108 may include an alternating current power supply (not shown).

The electrodes 110 are shown disposed within the field of bristles 104, which construction provides the advantage of generating chemical agents at the application site where the toothbrush contacts a user's teeth and where a concentration of a dentifrice is likely to be located during use. Further, locating the electrodes in close proximity to each other within the field of bristles creates a localized electric field between the electrodes during use that is unlikely to be contacted by the user, but that will likely encounter saliva and the dentifrice. It is understood, however, that electrodes 110 may be located elsewhere about the toothbrush, such as along the neck below the bristles, and that multiple sets of electrodes may be used. It is further understood that toothbrush 100 may include cleaning elements other than bristles, and that the electrodes may be incorporated into the alternative cleaning elements (e.g., an upstanding wall made of an electrically conductive polymer). It is further understood that the electrodes may be formed as cleaning elements or portions of cleaning elements. For instance, the electrodes may form bristles or other cleaning elements or may form portions of cleaning elements, such as a base portion of a bristle.

As shown in FIG. 2, electrodes 110 are relatively short in comparison with the height of bristles 104, which can reduce the possibility of user contact with the electrodes. The possibility of user contact with the electrodes during use can be kept low by keeping the electrodes short and by surrounding them with bristles or another structure that limits user contact. Although it may not be necessary to limit user contact with the electrodes during use, such as for low-voltage configurations, it may be desirable to do so to avoid user discomfort from perceiving the electrical potential. User contact with the electrodes may also be reduced in other ways, such as by embedding them in a recess in the toothbrush head or by placing them in a channel through the head through which the electrolyte may pass, such as in the configuration shown in FIGS. 10A-10C.

Figure 3:
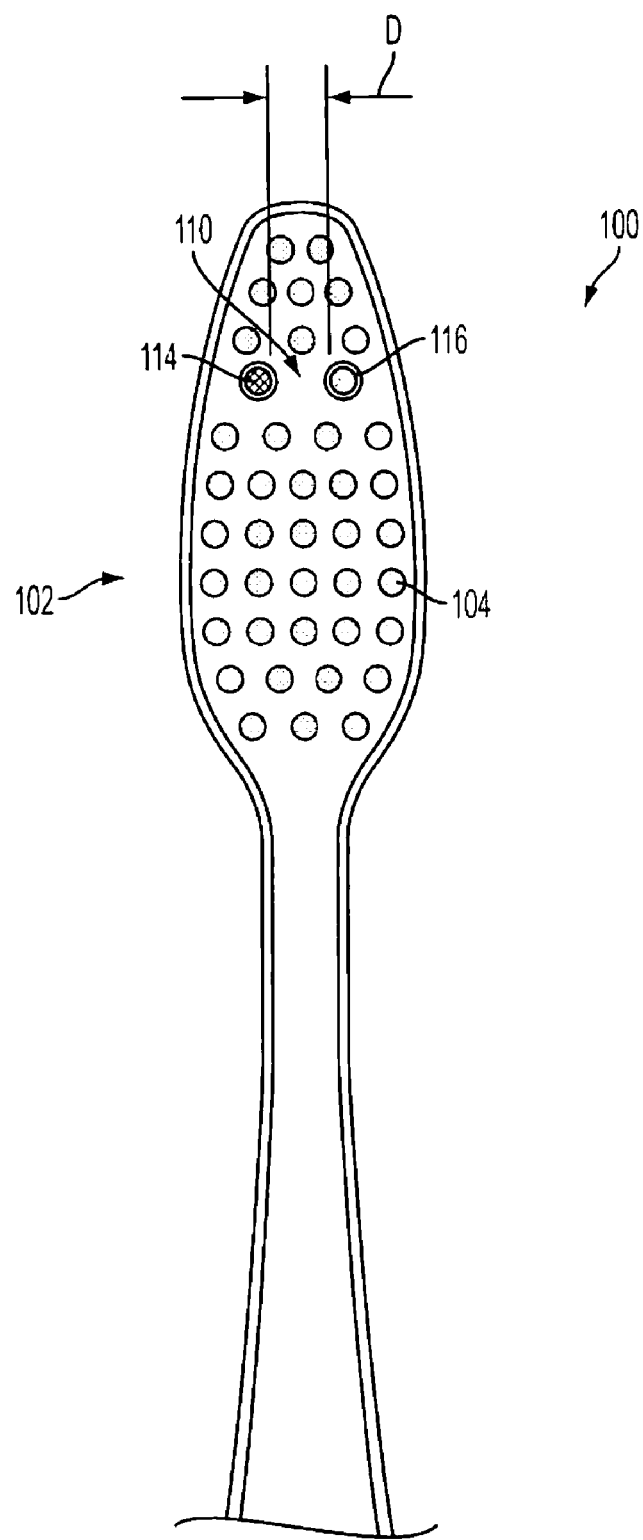
FIG. 3 is a front view of the head portion of the toothbrush of FIG. 1.

As shown in FIG. 3, cathode 114 and anode 116 are spaced apart a distance D. In one configuration, the distance D is 0.1 mm to 10 mm, an applied voltage therebetween is 0.2 volts to 400 volts, and the electrodes have an exposed, superficial surface area of 0.2 square centimeters to 5 square centimeters. Such a configuration can provide a beneficial current density between the electrodes of 3000 amperes per square centimeter to 30,000 amperes per square centimeter depending on ion conductivity of the electrolyte, which may be 0.1 siemens per meter to 100 siemens per meter and is preferably 0.2 siemens per meter to 100 siemens per meter. In one preferred configuration, the distance D is 1.5 to 3.5 mm for use with an applied voltage of 0.2 to 9 volts while in the presence of an electrolyte having a conductivity of 0.4 to 10 siemens per meter. Such a configuration can provide beneficial quantities of one or more oxidizing agents, depending on factors like electrolyte composition.

In operation, an electrical potential is provided across electrodes 110 to generate a localized electric field therebetween. A circuit is completed while the electrodes are in contact with electrolyte 124 (see FIG. 4), which conducts electricity between cathode 114 and anode 116. As cathode 114 is connected to negative line 120, it has a negative charge that supplies electrons to electrolyte 124 and it therefore attracts positively charged molecules. Similarly, anode 116 is connected to positive line 118 and has a positive charge that attracts electrons, which therefore attracts negatively charged molecules. The electrolyte permits a closed electrical circuit by providing charged molecules (ions) to the electrodes and/or by transporting electrons from the cathode to the anode.

The electrodes 110 may be made of metal, such as copper, steel or platinum, or another conductive material, such as semiconductors, graphite, graphite felt materials, glassy carbon materials, organic conductive materials, silver chloride, or polymeric conductive materials, etc. Further, electrodes 110 may include relatively non-conductive materials along with one or more conductive regions. For instance, a base material like a polymer may be coated with a more conductive material, such as a graphite felt. In another example, a conductive material like a copper wire may be embedded or placed on a support material, such as a larger polymeric structure. Both electrodes may be made from the same material or they may be made from different materials and/or have different configurations.

In one configuration, anode 116 is made from a mixed metal oxide or a heavy metal oxide that can decrease or eliminate the production of chlorine gas during use with an electrolyte that includes chloride ions or compounds involving chlorine atoms in various forms. Although chlorine in aqueous solutions, such as in the form of chlorous acid, can be a powerful disinfecting and oxidizing agent, chlorine gas can be harmful and can produce an undesirable odor. It may be desirable to avoid the production of chlorine gas while permitting chlorine to exist in an aqueous solution in the user's mouth to assist with cleaning and/or whitening the user's teeth. As such, anode 116 may include a heavy metal oxide to reduce or eliminate chlorine gas production, such as titanium dioxide that liberates the salt $Ti^+$ when an electric charge is applied across the electrodes. Further, the electrolyte may include chlorous acid or may generate it during application of the electric charge. A heavy metal salt, such as $Ti^+$, can act as a Lewis acid to bond with chlorine atoms to avoid generating chlorine gas. For instance, the $Ti^+$ can combine with chlorine atoms to create titanium tetrachloride. Although the titanium tetrachloride may subsequently react with water in the user's mouth to create hydrochloric acid, the production of chlorine gas will nonetheless be avoided. In addition, hydrochloric acid may be beneficial for cleaning the user's teeth and/or penetrating tooth enamel.

In another configuration, anode 116 is made from a glassy carbon material, such as a glassy carbon rod, which can also decrease or eliminate the production of chlorine gas when used with an electrolyte that includes chloride ions or compounds involving chlorine atoms in various forms. Glassy carbon is a non-graphitizing, dense type of carbon that is generally impermeable to gases, such as chlorine gas, and is relatively inert. As such, glassy carbon can be particularly advantageous for reductive dechlorination of chloride substances in the dentifrice by accepting electrons therefrom when used as anode 116. Thus, beneficial chemical agents that include chloride atoms, such as hydrochloric acid or chlorous acid, can be used for their intended disinfecting and oxidizing advantages without generating significant quantities of chlorine gas, if any.

Figure 4:
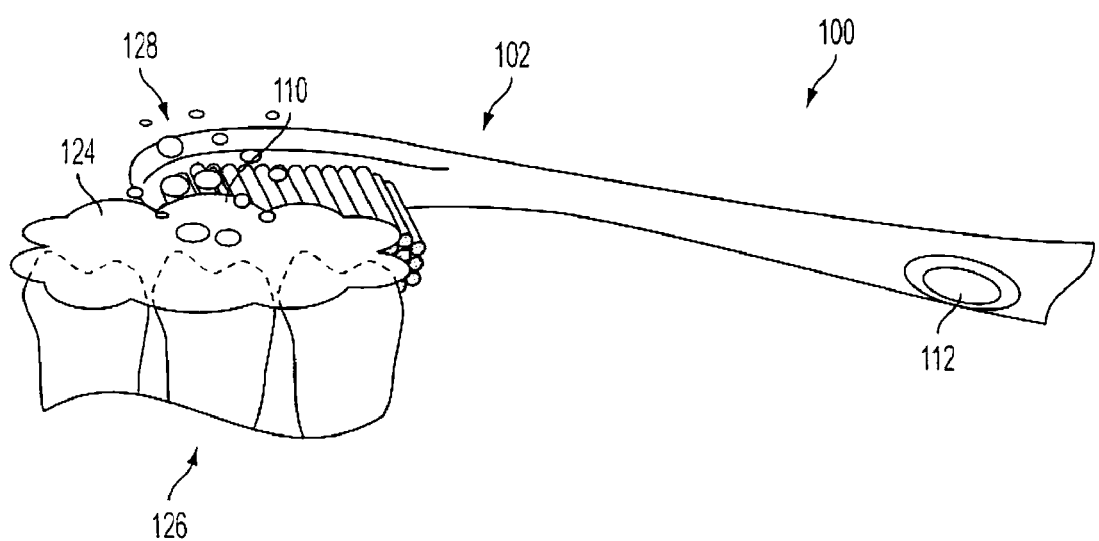
FIG. 4 is perspective view of the head portion of the toothbrush of FIG. 1 and a user's teeth illustrating a use of the toothbrush.

FIG. 4 illustrates use of toothbrush 100 for cleaning and/or whitening a user's teeth 126. In a low voltage configuration, toothbrush 100 may be used to generate chemical agents via electrolysis of an electrolyte that includes saliva and optionally other substances. The agents to be generated depend on the composition of electrolyte 124 and the charge applied thereto. As an example, applying an electrical potential of 0.5 to 1.1 volts or more across electrodes 110 using a glassy carbon material for anode 116 in the presence of saliva generates hydrogen gas at cathode 114 and oxygen gas at anode 116 via known principles of water electrolysis. Oxygen gas provides health benefits to the user's gums and provides a perception of freshness to the user. In addition, oxygen is a weak oxidizer that provides sanitizing and bleaching benefits to the user's teeth 126. Further, both the hydrogen gas and the oxygen gas create bubbles 128 that provide a sensory perception to the user as the bubbles hit the user's gums.

In addition to hydrogen and oxygen, other chemical agents can be generated from the application of a 1.5-volt potential difference depending on the composition of electrolyte 124. For example, if electrolyte 124 is a dentifrice, such as aqueous toothpaste, containing potassium chloride or sodium chloride, chlorine gas or hypochlorite can be generated in the user's mouth. When the electrical potential is applied to electrolyte 124, the negatively charged chlorine ion thereof receives an electron at cathode 114 to form chlorine gas or hypochlorite (also known as hypochlorous acid). If sodium chloride is present, sodium hypochlorite may be generated, which is commonly known as household bleach. Chlorine gas, hypochlorite and sodium hypochlorite provide whitening, sanitizing and potentially deodorizing benefits to the user's mouth.

It is understood that may other compounds may be used in electrolyte 124 to generate beneficial chemical agents. As another example, the presence of calcium carbonate in electrolyte 124 may permit calcium to be produced, which can strengthen a user's teeth. Many of these compounds are salts that provide the added benefit of improving the electrical conductivity of electrolyte 124 compared with water alone. The presence of salts in the electrolyte improves the rate of the electrolysis of water and the overall effectiveness of the electrodes, which increases the rate of oxygen and hydrogen production. Salts or other conductivity-affecting agents may be added to the electrolyte that are not used for producing chemical agents, but which affect conductivity of the electrolyte, such as to improve conductivity.

In a high voltage configuration, the single set of electrodes 110 can generate ozone ($H_2O_2$) from an aqueous electrolyte 124. For example, the application of about nine volts or more across electrodes 110 can generate ozone from saliva alone or from an aqueous electrolyte containing a salt. Ozone is a powerful oxidizer that is effective for bleaching teeth 126 and for disinfecting the user's mouth. Ozone is produced from the discharge of electricity in the presence of oxygen. Thus, toothbrush 100 can generate ozone by initially producing oxygen via the electrolysis of water when an electrical potential is provided to electrodes 110. Ozone is subsequently produced when the same charge is applied to the oxygen. A higher voltage is used for a single set of electrodes that both electrolyzes water to generate oxygen and that charges the oxygen to produce ozone than is used by a single set of electrodes that only performs one of these functions. As discussed below, lower voltages may be used in configurations having multiple sets of electrodes that cooperate to electrolyze water and produce ozone.

Depending upon its composition, the single set of electrodes 110 can generate hydrogen peroxide from an aqueous electrolyte 124 in the high voltage configuration. For instance, hydrogen peroxide can be generated from the application of a nine-volt electrical potential in the presence of aqueous sulphuric acid ($H_2SO_4$) or acidic ammonium bisulphate ($NH_4HSO_4$). In this process, electrolysis of electrolyte 124 containing one of these substances produces peroxydisulfate (($SO_4)_2$). Hydrolysis of the peroxydisulfate, in which the molecule is cleaved into two parts by the addition of a molecule of water, generates hydrogen peroxide ($H_2O_2$). Hydrogen peroxide is also a powerful oxidizer that is effective for bleaching teeth 126 and for disinfecting the user's mouth.

Generating powerful oxidizers such as ozone and hydrogen peroxide in situ can provide many advantages. One advantage is that these substances do not need to be stabilized for storage, as they are utilized when they are created. This can be advantageous due to the unstable nature of these substances. For instance, ozone is highly unstable and naturally decays into ordinary oxygen through the reaction $2O_3 \rightarrow 3O_2$, which makes it difficult to store for future use. Further, hydrogen peroxide can spontaneously decompose into water and oxygen gas: $2H_2O_2 \rightarrow 2H_2O+O_2+$Energy. The rate of its decomposition depends on temperature and the concentration of the peroxide, as well as the presence of impurities and stabilizers. As peroxide is incompatible with many substances and its decomposition can be accelerated from various catalysts, it can be difficult to produce a composition for long term storage that will have a high concentration of peroxide when it is used. For example, it can be difficult to manufacture a dentifrice that can maintain a desired concentration of peroxide after prolonged storage. Many conventional dentifrices are designed to provide multiple functions, such as removing tartar, freshening breath, killing bacteria, applying fluoride to teeth and generally cleaning teeth. As such, dentifrices may include compounds directed to other purposes that can be incompatible with the storage of peroxides.

Figure 5:
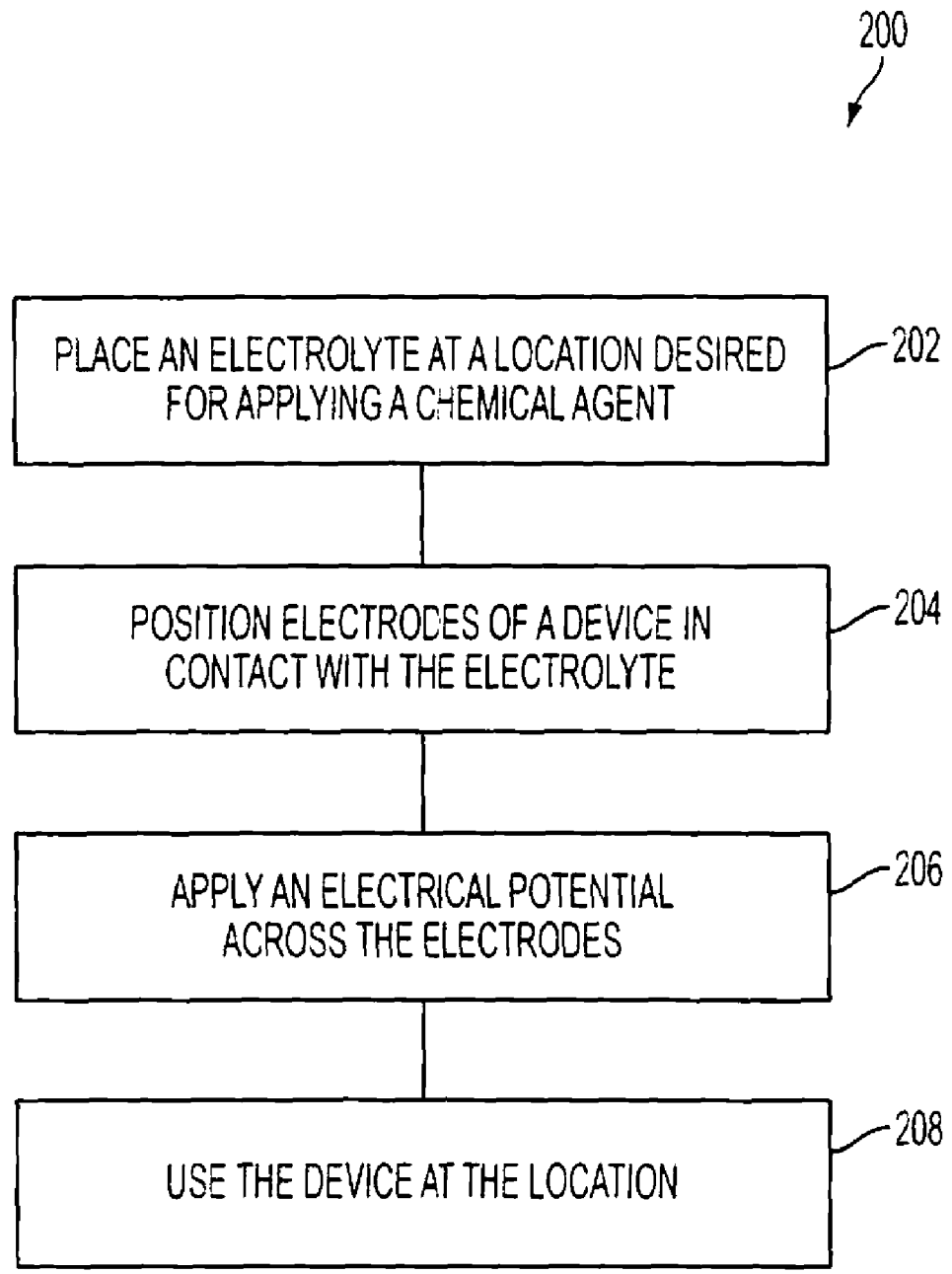
FIG. 5 is a flow diagram illustrating a method for generating a chemical agent in situ according to an embodiment of the invention.

Referring now to FIG. 5, a method 200 is shown for generating a chemical agent in situ according to an embodiment of the invention. Method 200 will be discussed using the example toothbrush 100 discussed above. However, it is understood that method 200 may be practiced with a wide variety of devices.

As shown, method 200 includes step 202 of placing an electrolyte at a location desired for applying a chemical agent. The electrolyte can be any substance that conducts electricity in solution, such as a liquid, a gel or even a solid, and that is appropriate for the desired location and chemical agent to be generated. For instance, merely salivating can provide an appropriate electrolyte to a desired location (the user's mouth). Step 204 includes positioning electrodes of a device, such as electrodes 110, into contact with the electrolyte. Step 206 includes applying an electrical potential across the electrodes while the electrodes are in contact with the electrolyte. This results in the generation of a chemical agent at a location at which it is to be used. As shown in step 208, the device can be used at the desired location along with the generated chemical agent. Thus, the agent is produced in situ and can be used immediately.

Figure 6:
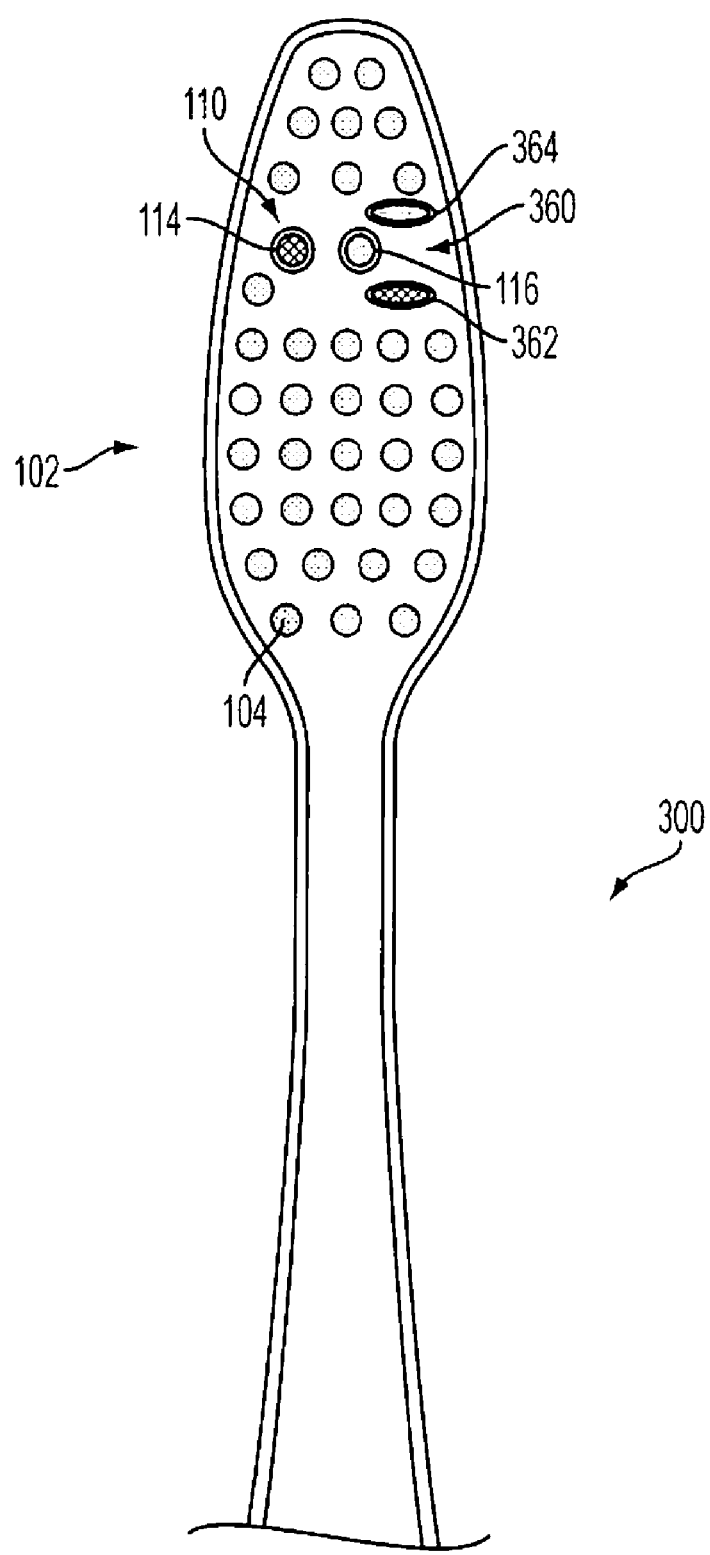
FIG. 6 is a front view of a head portion of a toothbrush according to another embodiment of the invention.

Referring now to FIG. 6, a toothbrush 300 is shown for supporting one or more aspects of the invention. Toothbrush 300 generally includes the same aspects as toothbrush 100, except as discussed below. Toothbrush 300 differs from toothbrush 100 in that it includes a second set of electrodes 360 disposed proximate anode 116. Electrodes 360 include a cathode 362 and an anode 364, which are respectively connected to a negative side and a positive side of voltage source 108. As such, cathode 362 has a negative charge during use and anode 364 has a positive charge. Many different configurations of electrodes are possible, however, placing electrodes 360 proximate to anode 116 where oxygen is generated permits toothbrush 300 to generate ozone at low voltages. This is because second set of electrodes 360 can apply an electric charge directly to oxygen generated at anode 116 during the electrolysis of water. This permits ozone to be produced without requiring the higher voltages needed to both electrolyze water and to produce ozone from a single set of electrodes.

As an example, an electrical potential of about 1.5 volts or more can be applied to electrodes 110 in the presence of an aqueous electrolyte containing a salt. This results in the production of oxygen at anode 116. Ozone can be produced by applying an electric charge of about 0.7 volts or more to the oxygen created at anode 116. Thus, ozone can be created in a user's mouth with toothbrush 300 using a small electrical charge. Keeping the applied voltage low can reduce the possibility of the user perceiving the applied electrical charge, which may be undesirable for many users. Further, keeping the voltage requirements low for toothbrush 300 permits a small capacity voltage source to be used and permits the voltage source to have a longer life than would be possible in a higher voltage configuration.

Due to the different electrical potentials provided to electrodes 110 and 360, a resistor or other voltage regulation device may be included in toothbrush 300 to provide a smaller electrical potential to electrodes 360 than is provided to electrodes 110. It is understood that other voltage configurations are possible for alternative configurations and that electrodes 110 and 360 could have the same electrical potential applied to them (e.g., 1.5 volts could be applied to both sets of electrodes to electrolyze water and generate ozone). Optionally, switch 112 shown in FIGS. 1 and 2 may include a first position for only activating electrodes 110 at a first voltage (e.g., a low voltage), and it may include a second position for activating electrodes 110 at a second voltage (e.g., a high voltage). It may also include a third position for activating electrodes 360 at a third voltage along with electrodes 110 at a fourth voltage.

Figure 7:
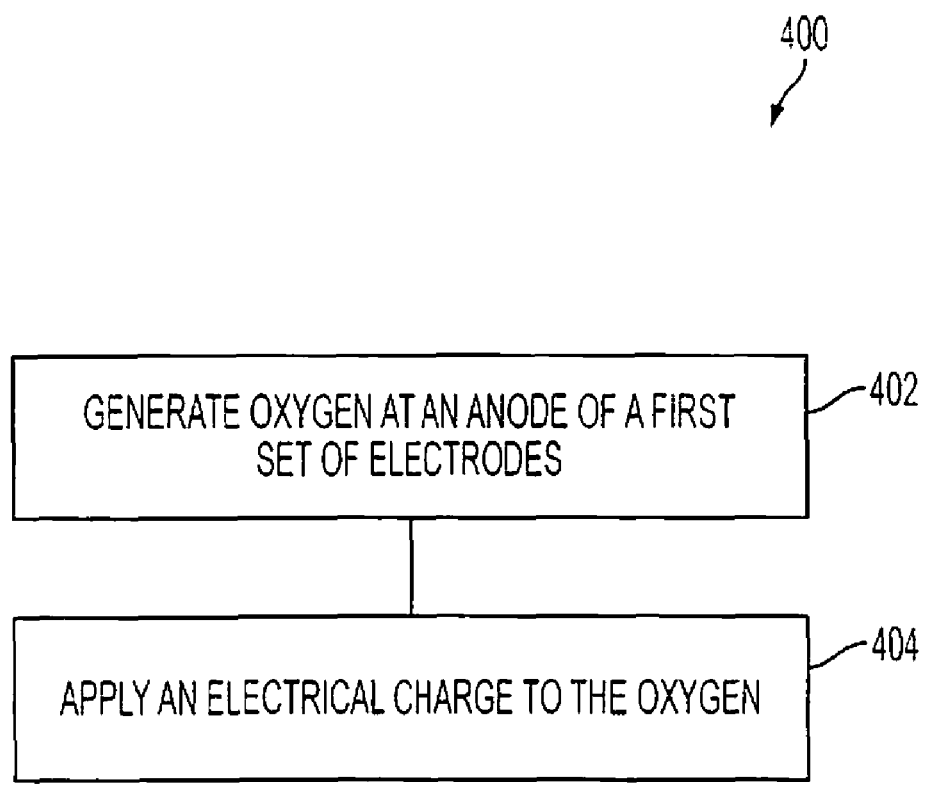
FIG. 7 is a flow diagram illustrating a method for generating ozone in situ according to a further embodiment of the invention.

Referring now to FIG. 7, a method 400 is shown for generating ozone in situ according to a further embodiment of the invention. Method 400 will be discussed using the example toothbrush 300 discussed above. However, it is understood that method 400 may be practiced with a wide variety of devices. As shown, method 400 includes the step 402 of generating oxygen at an anode 116 of a first set of electrodes 110, which may be accomplished via electrolysis of water. The method further includes the step 404 of applying an electrical charge to the oxygen, which may be accomplished via a second set of electrodes 360 proximate the anode. This results in converting oxygen into ozone, which is generated in a user's mouth for immediate use.

Figure 8A:
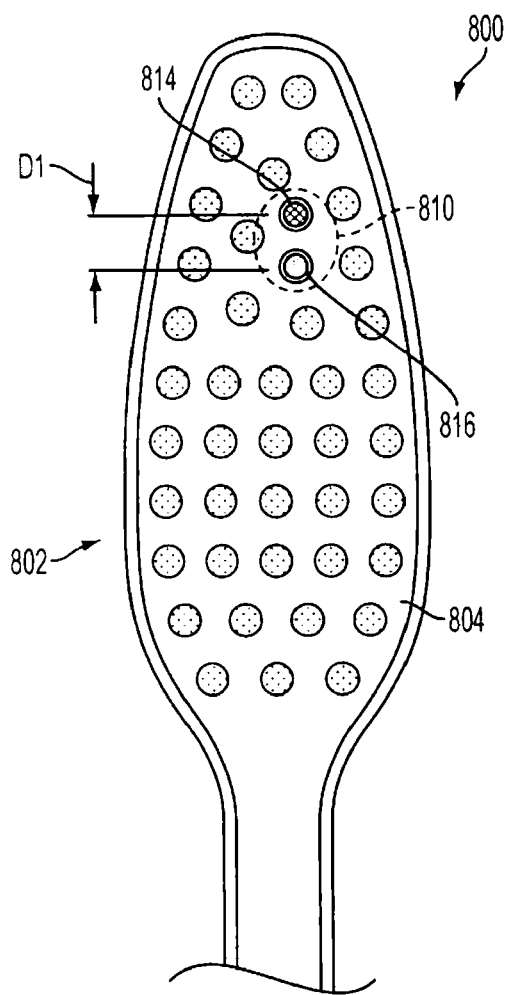
FIG. 8A is a front view of a head portion of a toothbrush according to a further embodiment of the invention.

Referring now to FIG. 8A, a toothbrush 800 is shown for supporting one or more aspects of the invention. Toothbrush 800 generally includes a head 802 and the same aspects as toothbrush 100, except as discussed below. Toothbrush 800 differs from toothbrush 100 in that electrodes 810 are longitudinally oriented in an arrangement substantially parallel with a longitudinal axis of the handle. Thus, as shown, electrodes 810 include a cathode 816 spaced apart from an anode 814 by a distance D1, which may generally be the same as distance D of FIG. 3. Such an arrangement may be beneficial for embedding the electrodes more fully within the field of bristles or other cleaning elements 804 than the configuration of FIG. 3.

Figure 8B:
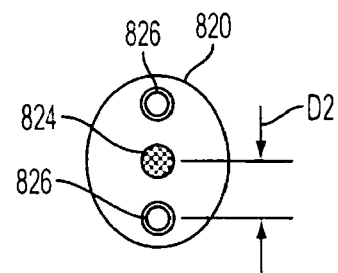
FIGS. 8B-8D are front views of electrode configurations of the head portion of FIG. 8A according to additional embodiments of the invention.
Figure 8C:
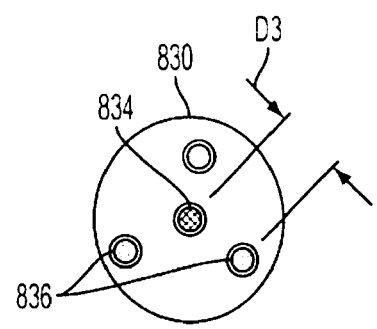

FIGS. 8B through 8C illustrate alternative electrode configurations that may be used with toothbrush 800, either alone or in combination with other sets of bristles. Each of these configurations show a single anode in an arrangement with multiple cathodes. However, opposite configurations in which a single cathode is arranged with multiple anodes may also be practiced. Further, rather than a single anode or cathode, multiple anodes or cathodes may also be arranged with multiple oppositely-charged electrodes to provide various beneficial arrangements. In addition, alternating-current embodiments of toothbrush 800 may be practiced with these and other configurations, such that oppositely-charged electrodes cycle between having positive and negative charges and/or different levels of positive and/or negative charges.

The configuration of FIG. 8B includes a pair of cathodes 826 disposed about an anode 824 by a distance D2, which may generally be the same as distance D of FIG. 3. The pair of cathodes 826 may be on opposite sides of anode 824 and may generally be longitudinally oriented substantially parallel with a longitudinal axis of the handle. However, the pair of cathodes and their orientation may configured in different arrangements. The configuration of FIG. 8B provides a compact arrangement of electrodes 820 that may be placed near the center of bristle field 804. The configuration of FIG. 8B or similar configurations using a plurality of cathodes disposed about an anode can increase the size of the electric field between oppositely charged electrodes via the plurality of cathodes.

The configuration of FIG. 8C includes three cathodes 836 disposed about an anode 834 by a distance D3, which may generally be the same as distance D of FIG. 3. The cathodes may be disposed the same distance D3 from the anode, or they may have variable spacing from the anode. Different distances between each cathode and the anode can provide electric fields of various strengths therebetween, which may be beneficial for producing different agents and/or different concentrations of the agents between the differently-spaced cathode-anode sets. The configuration of FIG. 8C also provides a compact arrangement of electrodes 830 that may be placed near the center of bristle field 804.

Figure 8D:
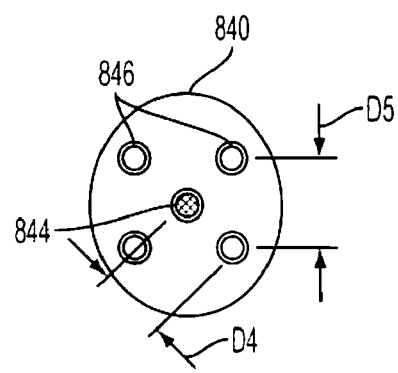

The configuration of FIG. 8D includes four cathodes 846 disposed about an anode 844 by a distance D4, which may generally be the same as distance D of FIG. 3. The cathodes may be disposed the same distance D4 from the anode, or they may have variable spacing from the anode. Preferably, the distance D4 is less than the spacing between adjacent cathodes D5 to ensure sufficient electric field strength for each cathode-anode set. The configuration of FIG. 8D also provides a compact arrangement of electrodes 840 that may be placed near the center of bristle field 804.

Figure 9A:
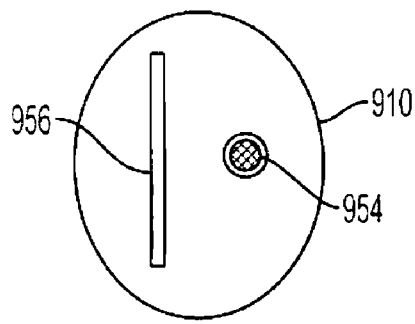
FIGS. 9A-9E are front views of electrode configurations of the head portion of FIG. 8A according to yet additional embodiments of the invention.
Figure 9B:
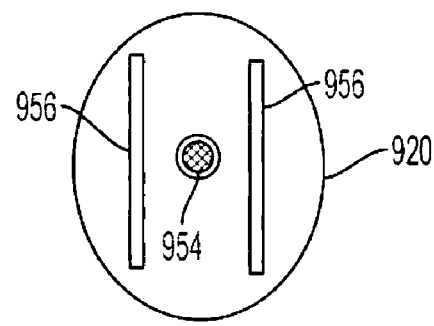
Figure 9C:
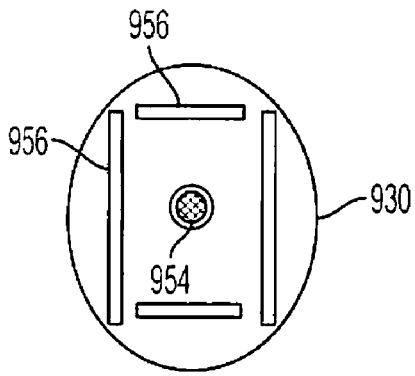

FIGS. 9A through 9E illustrate additional electrode configurations 910, 920, 930, 940, 950 that may be used with toothbrush 800, either alone or in combination with other sets of bristles. These configurations have generally the same aspects as FIGS. 8A through 8C, except as discussed below. FIGS. 9A through 9C illustrate various configurations 910, 920, 930 that may be placed partially or completely within bristle field 804 of FIG. 8A. The configurations of FIGS. 9A through 9C include a generally columnar first electrode 954, which as shown is an anode, as well as one or more electrode walls 956, which as shown are cathodes. The use of electrode walls can be advantageous for increasing the size of the electric field between oppositely charged electrodes and may, therefore, increase the quantity of chemical agents generated therein during use of the toothbrush.

Figure 9D:
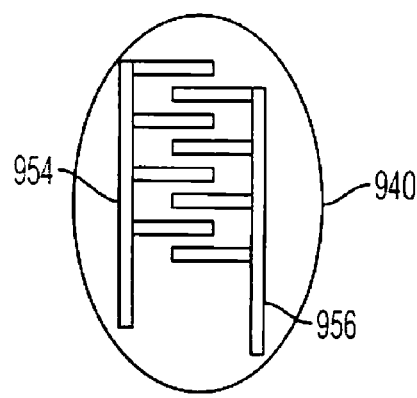

FIG. 9D illustrates the use of electrode walls for both of the oppositely-charged electrodes, which can further increase the size of the electric field therebetween. The configuration shown in FIG. 9D is an interlocking configuration 940 in which anode walls 954 are partially interposed with cathode walls 956 in a closely-spaced arrangement. Such a configuration can provide high field strength electric fields between the oppositely charged electrodes, as well as provide large surface areas between the electrodes to form large electric fields.

Figure 9E:
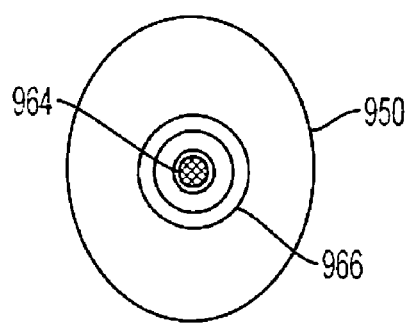

FIG. 9E illustrates a circular configuration 950 between electrodes in which a first electrode (e.g., columnar anode 964) is partially or fully surrounded by one or more second electrodes (e.g., cylindrical cathode 966). Such a configuration can provide a high field strength electric field between the electrodes. In addition, such a configuration can be effective for containing the electric field between the electrodes to avoid inadvertent contact with tissue in the user's mouth.

Figure 10A:
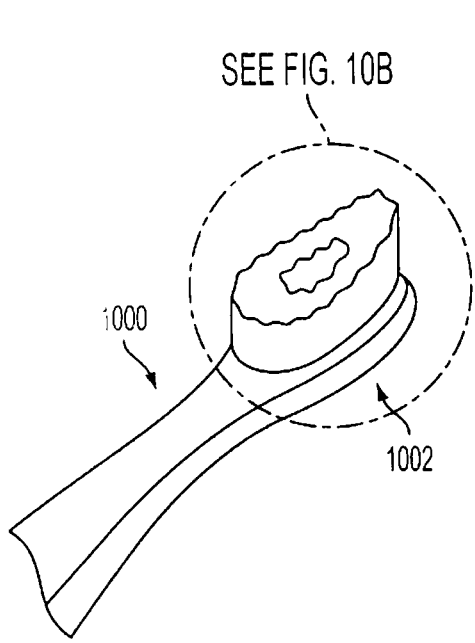
FIG. 10A is a front perspective view of a head portion of a toothbrush according to a further embodiment of the invention.
Figure 10B:
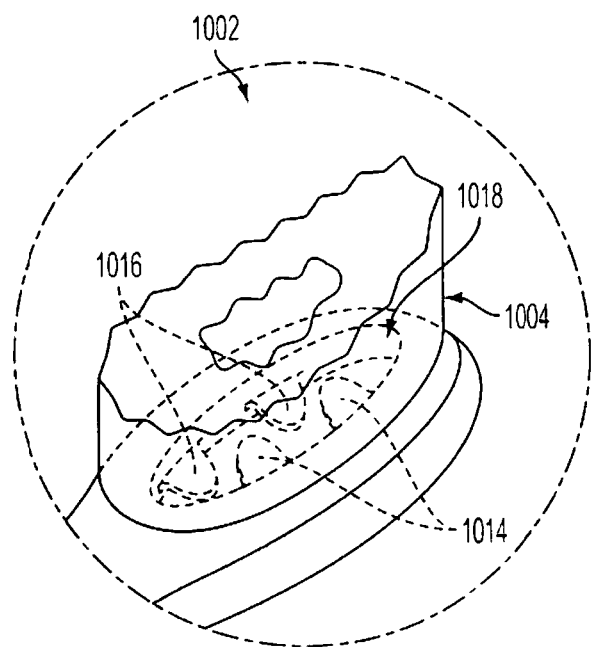
FIG. 10B is a close view of the head portion of FIG. 10A.
Figure 10C:
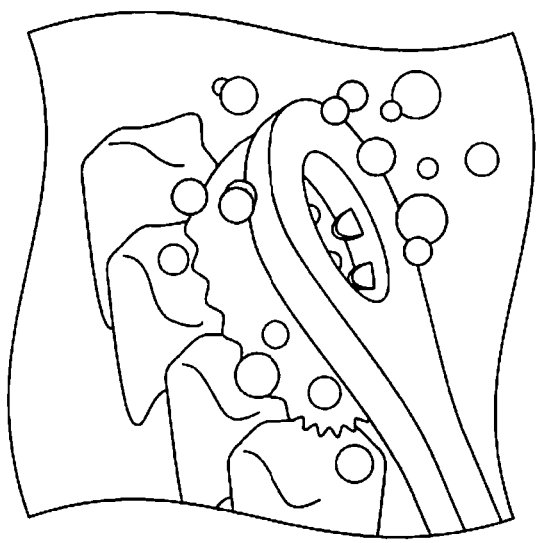
FIG. 10C is a rear perspective view of the head portion of FIG. 10A.

Referring now to FIGS. 10A through 10C, a toothbrush 1000 is shown for supporting one or more aspects of the invention. Toothbrush 1000 generally includes the same aspects as toothbrushes 100 and 800, except as discussed below. Toothbrush 1000 differs from toothbrushes 100 and 800 in that electrodes 1014 and 1016 are disposed within a channel 1018 formed through the toothbrush head 1002. Channel 1018 can enhance the flow of saliva and dentifrice past the electrodes during use and, thereby, increase the quantity of agents being generated compared to configurations lacking the channel. Preferably, one side of the channel is disposed within a field of cleaning elements 1004 such that the agents are generated in situ within the field of cleaning elements near the application location. As an example, FIG. 10C illustrates chemical agents being generated within the field of cleaning elements 1004 at the location of use on the user's teeth. Such a configuration can also be beneficial for avoiding contacting between tissue in the user's mouth and the electrodes and the electric fields therebetween, as well as limit the electric fields to a region within the toothbrush head.

While the present invention has been described in connection with the illustrated embodiments, it will be appreciated and understood that modifications may be made without departing from the true spirit and scope of the invention. In particular, the invention may apply many different devices and/or methods for using the same.

What is claimed is:

1. An oral care device for generating a chemical agent in situ outside of the oral care device, comprising:
    a head portion comprising a field of cleaning elements; a voltage source;
    a first set of electrodes disposed on the head portion within the field of cleaning elements and electrically connected to the voltage source, the first set of electrodes comprising a first cathode and a first anode, the first cathode and the first anode having a first electrical potential therebetween when receiving an electric charge from the voltage source; and
    a second set of electrodes disposed on the head portion and electrically connected to the voltage source, the second set of electrodes comprising a second cathode and a second anode, the second cathode and the second anode having a second electrical potential therebetween when receiving an electric charge from the voltage source, the second set of electrodes being disposed about the first anode;
    wherein the chemical agent is formed in situ upon contact with an aqueous electrolyte when the first electrical potential is applied
    wherein the first electrical potential is different from the second electrical potential.

2. The oral care device of claim 1, wherein the second electrical potential is 0.7 volts or more.

3. The oral care device of claim 1, further comprising a voltage selector having a plurality of voltage settings selectable by a user.

4. The oral care device of claim 3, wherein the voltage settings comprise: a first voltage setting to provide a first electrical potential to the first set of electrodes without applying an electrical potential to the second set of electrodes; and a second voltage setting to provide a second electrical potential to the second set of electrodes while applying the first electrical potential to the first set of electrodes.

5. The oral care device of claim 4, wherein the voltage settings further comprise a third voltage setting to provide a third electrical potential to the first set of electrodes without applying an electrical potential to the second set of electrodes.

6. The oral care device of claim 1, wherein the first anode produces oxygen in situ while the first set of electrodes is in contact with the aqueous electrolyte and is receiving an electric charge from the voltage source, and the second set of electrodes produces an oxidizing agent from the oxygen, and wherein the oxidizing agent includes ozone.

7. The oral care device of claim 1, wherein the first electrical potential is 1.5 volts or more.

8. The oral care device of claim 1, wherein the first electrical potential is less than 0.7 volts.

9. The oral care device of claim 8, wherein the first electrical potential is 0.25 to 0.55 volts.

10. The oral care device of claim 1, wherein the first set of electrodes are configured to suppress the production of chlorine while forming the chemical agent.

11. The oral care device of claim 10, wherein the first set of electrodes comprises a metal oxide.

12. The oral care device of claim 11, wherein the metal oxide comprises titanium dioxide.

13. The oral care device of claim 10, wherein the first anode of the first set of electrodes comprises glassy carbon.

14. The oral care device of claim 1, wherein the head portion comprises more cathodes than anodes.

15. The oral care device of claim 1, wherein the first cathode forms an interlocking arrangement with the first anode.

16. The oral care device of claim 1, wherein the first anode and first cathode have different shapes.

17. The oral care device of claim 16, wherein one of the electrodes is generally columnar and one of the electrodes is wall-shaped.

18. The oral care device of claim 17, further comprising a plurality of wall-shaped electrodes.

19. The oral care device of claim 1, wherein the first set of electrodes is disposed in an open channel on the head portion.

20. A toothbrush for generating an oxidizing agent in situ, the toothbrush comprising:
    a voltage source configured to provide an electrical potential;
    a head;
    a field of cleaning elements on a face of the head;
    a first set of electrodes having a first anode and a first cathode extending outwardly from the face of the head and disposed within the field of cleaning elements, the first set of electrodes being configured to generate a localized electric field between the first anode and the first cathode while receiving an electrical potential from the voltage source and to generate an oxidizer in situ when an electrolyte contacts the electric field; and
    a second set of electrodes disposed on the head and electrically connected to the voltage source, the second set of electrodes comprising a second cathode and a second anode, the second cathode and the second anode having a second electrical potential therebetween when receiving an electric charge from the voltage source, the second set of electrodes being disposed about the first anode
    wherein the first electrical potential is different from the second electrical potential.

21. The toothbrush of claim 20, wherein the electrical potential is 9 volts or more, the electrolyte comprises water, and the oxidizer is one of ozone and hydrogen peroxide.

22. The toothbrush of claim 20, wherein the electrical potential is less than 0.7 volts.

23. The toothbrush of claim 22, wherein the electrical potential is 0.25 to 0.55 volts.

24. The toothbrush of claim 20, wherein the second set of electrodes are arranged to generate an oxidizer in situ using oxygen produced at the anode of the first set of electrodes when receiving an electrical potential.

25. The toothbrush of claim 24, wherein the oxidizer comprises ozone.

26. An oxidizing agent generator for generating an oxidizing agent in situ, the oxidizing agent generator comprising:

a first portion arranged to contact an electrolyte disposed outside of the oxidizing agent generator and proximate the application site for the oxidizing agent;

a voltage source for providing an electrical potential;

a first set of electrodes having a first electrical potential therebetween disposed on the first portion and electrically connected to the voltage source for generating an oxidizing agent when receiving an electrical potential from the voltage source, the oxidizing agent selected from the group consisting of hydrogen peroxide and ozone;

a second set of electrodes having a second electrical potential therebetween disposed about an anode of the first set of electrodes, the second set of electrodes arranged to generate an oxidizer when receiving an electrical potential from the voltage source; and wherein the first electrical potential is different from the second electrical potential.

27. The oxidizing agent generator of claim 26, wherein the electrical potential is 9 volts or more and the electrolyte comprises water.

28. The oxidizing agent generator of claim 26, wherein the oxidizing agent generator is an oral care device.

29. The oxidizing agent generator of claim 28, wherein the oxidizing agent generator further comprises cleaning elements on the first portion and the first set of electrodes are disposed proximate the cleaning elements.

30. The oxidizing agent generator of claim 29, wherein the electrolyte comprises water the second set of electrodes are arranged to generate the oxidizer when receiving the electrical potential from the voltage source using oxygen produced at the anode of the first set of electrodes.

31. The oxidizing agent generator of claim 30, wherein the oxidizer is ozone.

32. The oxidizing agent generator of claim 26, wherein the voltage source comprises one of a rechargeable battery and a capacitor.

33. An oral care device for generating a chemical agent in situ outside of the oral care device, comprising:

a head portion comprising a field of cleaning elements; a voltage source;

a first set of electrodes disposed on the head portion within the field of cleaning elements and electrically connected to the voltage source, the first set of electrodes comprising a first cathode and a first anode, the first cathode and the first anode having a first electrical potential therebetween when receiving an electric charge from the voltage source; wherein the chemical agent is formed in situ upon contact with an aqueous electrolyte when the first electrical potential is applied; and a second set of electrodes disposed on the head portion and electrically connected to the voltage source, the second set of electrodes comprising a second cathode and a second anode, the second cathode and the second anode having a second electrical potential therebetween when receiving an electric charge from the voltage source, the second set of electrodes being disposed about the first anode; wherein the first anode produces oxygen in situ while the first set of electrodes is in contact with the aqueous electrolyte and is receiving an electric charge from the voltage source, and the second set of electrodes produces an oxidizing agent from the oxygen.

34. The oral care device of claim 33, wherein the second electrical potential is 0.7 volts or more.

35. The oral care device of claim 33, further comprising a voltage selector having a plurality of voltage settings selectable by a user.

36. The oral care device of claim 35, wherein the voltage settings comprise: a first voltage setting to provide a first electrical potential to the first set of electrodes without applying an electrical potential to the second set of electrodes; and a second voltage setting to provide a second electrical potential to the second set of electrodes while applying the first electrical potential to the first set of electrodes.

37. The oral care device of claim 36, wherein the voltage settings further comprise a third voltage setting to provide a third electrical potential to the first set of electrodes without applying an electrical potential to the second set of electrodes.

38. The oral care device of claim 33, wherein the oxidizing agent includes ozone.

39. A toothbrush for generating an oxidizing agent in situ, the toothbrush comprising:

a voltage source configured to provide an electrical potential;

a head;

a field of cleaning elements on a face of the head; and a first set of electrodes having an anode and a cathode extending outwardly from the face of the head and disposed within the field of cleaning elements, the first set of electrodes being configured to generate a localized electric field between the anode and the cathode while receiving an electrical potential from the voltage source and to generate an oxidizer in situ when an electrolyte contacts the electric field;

wherein the electrolyte comprises water and the toothbrush further comprises a second set of electrodes disposed about the anode of the first set of electrodes, the second set of electrodes arranged to generate an oxidizer in situ using oxygen produced at the anode of the first set of electrodes when receiving an electrical potential.

40. The toothbrush of claim 39, wherein the oxidizer comprises ozone.

41. An oxidizing agent generator for generating an oxidizing agent in situ, the oxidizing agent generator comprising:

a first portion arranged to contact an electrolyte disposed outside of the oxidizing agent generator and proximate the application site for the oxidizing agent;

a voltage source for providing an electrical potential; and a first set of electrodes disposed on the first portion and electrically connected to the voltage source for generating an oxidizing agent when receiving an electrical potential from the voltage source, the oxidizing agent selected from the group consisting of hydrogen peroxide and ozone;

wherein the electrolyte comprises water and the oxidizing agent generator further comprises a second set of electrodes disposed about an anode of the first set of electrodes, the second set of electrodes arranged to generate an oxidizer when receiving an electrical potential from the voltage source using oxygen produced at the anode of the first set of electrodes.

42. The oxidizing agent generator of claim 41, wherein the oxidizing agent generator is an oral care device.

43. The oxidizing agent generator of claim 42, wherein the oxidizing agent generator further comprises cleaning elements on the first portion and the first set of electrodes are disposed proximate the cleaning elements.

44. The oxidizing agent generator of claim 41, wherein the oxidizer is ozone.

* * * * *